United States Patent [19]

Georgescu

[11] Patent Number: 5,601,805
[45] Date of Patent: Feb. 11, 1997

[54] METHOD OF CONDITIONING ENAMEL, DENTINE AND SIMILAR SUBSTRATES TO OBTAIN ADHESIVE BONDING OF POLYMERIC MATERIALS

[76] Inventor: Maria A. Georgescu, 19-28 Grove St., Ridgewood, N.Y. 11385

[21] Appl. No.: 394,460

[22] Filed: Feb. 27, 1995

[51] Int. Cl.⁶ .............................. A61K 7/24; A61K 6/00; C08L 15/00
[52] U.S. Cl. .............................. 424/55; 523/111; 523/120
[58] Field of Search .............................. 424/55; 523/111, 523/120

[56] References Cited

U.S. PATENT DOCUMENTS 3,897,548   7/1975   Katz ........................................ 424/54
5,133,957   7/1992   Suh et al. .................................. 424/49

Primary Examiner—Thurman K. Page
Assistant Examiner—Kathryne E. Shelborne
Attorney, Agent, or Firm—Kane, Dalsimer, Sullivan, Kurucz, Levy, Eisele and Richard

[57] ABSTRACT

A new conservative method of conditioning enamel, dentin and other similar substrates, for obtaining strong and durable adhesive bonding of polymeric materials is disclosed. The method of conditioning addresses both the inorganic and organic phases of the tooth and is based on the concept of formation of a unitary polymeric network comprising the tooth structure and the restorative material, including an intermediary smear layer chemically modified and transformed into a stable, uniform and porous layer by rubbing the tooth surface with an aqueous solution of mild polyfunctional organic acids (pH=1.2–3.5).

6 Claims, No Drawings

METHOD OF CONDITIONING ENAMEL, DENTINE AND SIMILAR SUBSTRATES TO OBTAIN ADHESIVE BONDING OF POLYMERIC MATERIALS

BACKGROUND OF THE INVENTION

1. Field of the Invention

The present invention relates to methods of conditioning substrates, particularly enamel and dentine, to obtain strong and durable adhesive bonding of polymeric materials.

2. Brief Description of Related Art

When a tooth looses its structural integrity, a restoration is necessary to maintain its biological functions.

The polymeric materials designed to replace the lost tooth tissue has to adhere perfectly to the tooth structure in order to avoid gaps and consequent leakage at the tooth—restoration interface.

The accomplishment of this requirement is difficult because of the following factors:

1. The tooth has a heterogeneous physical and chemical structure. The enamel as a hard protective tissue for the softer and vital dentinal tissue, is highly mineralized and inert, while dentine is a complex structure both inorganic and organic in nature, whose vitality is maintained by a continuous flow of the dentinal fluid. These structural differences entail differences in the capacity of adherence.

2. The adherent surface usually is not large enough to ensure a true adhesion by secondary forces.

3. The surface energy and consequently the surface wetability is too low for an intimate contact with the adhesive.

4. The smear layer left on the surface by mechanical preparation of the cavity, as well as the dentinal fluid, may interfere in the adhesion process.

5. The difference in the chemical nature between predominantly inorganic adherent surface and organic adhesive is not in favour of contact by chemical affinity.

6. The contraction stress induced by polymerization shrinkage may prevail over the adhesion strength.

To overcome the above impediments, the tooth surface has to be conditioned prior to any adhesive application.

The treatment of the tooth surface with conditioners is the crucial first step in the adhesion process, and consequently for restoration.

Heretofore the subject of conditioning was the mineral component of the tooth. The conditioner was a mineral acid ($HNO_3$ or $H_3PO_4$) or organic acid (citric acid, maleic acid or EDTA). These acids condition the tooth surface by an "etching" mechanism.

The effects of etching are: removal of the smear layer, removal of a superficial layer of the underlying sound structure, increasing surface area by pitting the enamel and opening the dentinal tubules, and increasing surface energy with a consequent increase of wetability.

The prior art etchant of choice for enamel is phosphoric acid.

This treatment was inconceivable for conditioning dentine, which is a vital, sensitive and complex structure.

The impractical protocol for the differential conditioning of enamel and dentine, as well as the lack of a milder acid as an alternative for $H_3PO_4$, led to the so-called "all-etch" technique using dilute (10–37%) $H_3PO_4$ solutions or gel on both enamel and dentine. This technique is used now in many bonding systems, in spite of its controversial benefits in bonding, in balance with its detrimental effects.

The detrimental effects of phosphoric acid even in concentrations of 10%, are well documented: loss of enamel of about 5–10 µm thickness, depth of enamel etch up to 50 µm, increase in dentine permeability and subsequent possible bacteria invasion. An increase in dentine wetness due to the toward flow of the dentinal fluid caused by the hypertonic 10–37% $H_3PO_4$ solutions, increased potential for pulpal irritation due to the mentioned hypertonicity, potential for denaturation of collagen and possible difference in depth of demineralization and depth of adhesive penetration and consequently the enamel or dentine weakness under the restoration are all appreciated in the art.

In an effort to find a milder acid equally efficient in conditioning both enamel and dentine, a great number of organic acids have been tried, such as: saturated organic acids e.g. formic, acetic, oxalic, succinic, unsaturated organic acids e.g. maleic, methacrylic, itaconic, citraconic, ascorbic; polyfunctional organic acids e.g. citric, lactic, malic, tartaric, pyruvic, glycine, alanine, ethylenediaminotetraacetic [EDTA].

Citric acid and EDTA are the only polyfunctional organic acids which found a practical use, due to their capacity of etching similar with that of $H_3PO_4$. (Gluma bonding system and Amalgam bond).

Since the micromechanical retention is well documented and an accepted mechanism of bonding, the target of conditioning was thought to be "well etching, well clean surface" to provide more and longer polymeric tags.

The newer concept of "hybrid layer" and its contribution in bonding, brought attention to the importance of the penetration of the adhesive into the micro spaces created by etching the tooth surface. The wetability of the tooth surface, which was considered a key factor in the adhesion process, proved to be a necessary condition, but insufficient if it is not associated with good penetration. Based on the latest experimental studies, wetability began to differentiate from penetration. The first as a physical process related to the difference in surface energy between adherent and adhesive, and the second as a diffusion process implying not only the physical structure of the adherent but also the chemical affinity between adherent and adhesive.

It was noticed that etching followed by a treatment ("priming") with a hydrophylic organic compound e.g. N-tolylglycine (NTG) and 2-hydroxy ethylmethacrylate (HEMA), may improve the adhesive penetration into the dentinal tubules and intertubular dentine and consequently the bonding strength. This treatment may be considered the second step of conditioning which addresses the organic phase of the tissue, while the first step, etching, is addressed to inorganic phase.

Complementing each other, the two conditioners facilitate the penetration of adhesive, perhaps not only by diffusion through permeabilized tissue but also by chemical affinity.

An attempt for a more conservative method of conditioning by preserving and modifying the smear layer is the use of a mixture of 2.5% nitric acid with either ferric or aluminum oxalate or phosphate-group containing methacrylates ("self-etching primers"). However the lower bond strength values than was expected, suggest, particularly for "self-etching priming", a poor adhesive penetration.

The present invention provides a conservative method of conditioning, able to improve the adhesive penetration and to yield equally strong and reliable bond strength for both enamel and dentine.

The new method of conditioning is conservative, preserving the smear layer. It allows for a minimum removal of the tooth structure during mechanical preparation of a cavity and improves the treatment of cervical erosions, root caries, decalcified tissue, accidental dental splits or fractures.

The new conditioners employed in the method of the invention are biocompatible, mild polyfunctional organic acids, usually found as constituents in plants, fruits and as metabolic intermediaries in the human body. The new conditioners may prevent pulp pathology, secondary caries and tooth sensitivity by their bacteriostatic effects.

The new conditioners are non-toxic and harmless for soft tissue. No special clinical precautions are necessary with their use.

The new method of conditioning is not an alternative for the known method of conditioning with $HNO_3$, $H_3PO_4$, EDTA, citric acid or maleic acid, but an improvement for adhesion of polymeric materials to the tooth structure in the most conservative and bacteriostatic manner.

SUMMARY OF THE INVENTION

The invention comprises, a process for conditioning a tooth structure to obtain a strong and durable adhesive bond to a polymeric material, which comprises;

mechanically preparing a tooth surface to receive the polymeric material, whereby a smear layer on the surface is formed;

applying to the smear layer, a conditioner which comprises a dilute aqueous solution of a carboxylic acid selected from the group consisting of hydroxy and amino carboxylic acids.

Polymeric materials conventionally employed in tooth restorations, when adhered to tooth surfaces conditioned in accordance with the process of the invention exhibit improved bonding strengths, thereby forming a more durable restoration.

The term "smear layer" is used herein in its commonly accepted sense as meaning the layer formed on a tooth surface from the debris or particles removed from a tooth structure during mechanical preparation of the cavity.

DETAILED DESCRIPTION OF THE INVENTION

The present invention distinguishes itself from the art described above, in that it exploits the capability of the mild polyfunctional organic acids to modify the smear layer and to transform it into a homogeneous, stable and porous layer, perfectly attached to the underlying tooth structure. Also, it produces a possible orientation of the collageneous and non-collageneous proteins as a dipole-dipole effect, orientation which may facilitate the subsequent penetration of the organic adhesive.

The most preferred inventive method for conditioning the surface of dentine and enamel for bonding polymeric materials consists in rubbing the surface for 5–10 seconds with the conditioner solution and leaving the layer of conditioner without agitation for an additional time of 15–20 seconds. Rubbing the surface is advantageous for the formation of a homogeneous, uniform modified smear layer and for its good attachment to the underlying structure.

The conditioners employed are polyfunctional organic acids in aqueous solutions of 0.5–2 molar concentrations (pH=1.2–3.5).

Representative of hydroxy and amino carboxylic acids which are employed as conditioners in the process of the invention are those of the general formula:

$$Y-R-COOH \quad \text{with } X \text{ on } R \tag{I}$$

wherein R is an aliphatic or aromatic hydrocarbon radical or a cyclic ether radical; X represents a hydroxy, primary amino or secondary amino group; and Y is hydrogen, alkyl, hydroxy-substituted alkyl, amino-substituted alkyl, carboxy-substituted alkyl, aldo or keto substituted alkyl, i.e.; alkyl wherein 2 hydrogen atoms on the same carbon have been substituted with a =O group. Preferred compounds of Formula I are those wherein the alkyl or substituted alkyl is lower alkyl of 1 to 8 carbon atoms and those having a plurality of hydroxyl and/or amino group substituents.

Also representative of the carboxylic acids are those of Formula I wherein R is heterocyclic, for example, the cyclic ethers glucuronic acid and galacturonic acid.

Preferred as the carboxylic acid conditioners of the invention are α-hydroxyl and α-amino carboxylic acids.

Ten organic acids were exemplified herein as most preferred: seven hydroxy acids (salicylic, lactic, glycolic, tartaric, gluconic, glucuronic, galac-turonic) and three amino acids (glycine, aspartic, glutamic). The adhesive used in the examples was the "primer" either of the commercially available Tenure® or of All Bond® bonding systems. The two mentioned bonding systems (Bowen's system; see U.S. Pat. No. 4,588,756 incorporated by reference thereto), have in common the "primer A" which is an acetonic solution of N-(p-tolyl)-glycineglycidylmethacrylate (NTG-GMA) and differ each other by "primer B" which is an acetonic solution of pyromellitic acid-dimethacrylate (PMDM) in Tenure®, and an acetonic solution of biphenyl-dimethacrylate (BPDM) in All Bond®. No difference in bond strength related to the two different "primers" was noted in the present application.

Other similar monomers may be used also as the adhesive for dentine and enamel conditioned in accordance with the invention.

The shear bond strengths on dentine and enamel produced by the same adhesive and different polyfunctional organic acids, in the range of 20–28 MPa are significantly higher than 18.45 and 18.34 MPa for Tenure® and respective All Bond® systems used as controls (see Table 2, infra), and than 7–15 Mpa for other bonding systems tested in parallel (Mirage®, Bond-it®, Denthesive®, Scotchbond MP®, Amalgambond®).

Correlating the chemical structure of the three elements in the adhesion process (tooth-conditioner-adhesive) with their properties and the shear bond strength values, one can assume:

The mechanism of conditioning the enamel and dentine with mild polyfunctional organic acids (Table 1, infra) is not simply etching but rather a superficial etching associated with chelation of calcium of hydroxy apatite and a new orientation of the proteinic molecules as a dipole-dipole effect.

The chelating capability of the α-hydroxy acids and α-amino acids is known: tartaric acid is used as a setting controller in glass-ionomers while EDTA and citric acid are used as conditioners of dentine and enamel. The etching effect produced by α-polyfunctional organic acids may vary with the solubility degree of their chelated products. The chelated products of EDTA, for example, are very stable but also very soluble in water such as the effect on enamel and dentine is a complete removal of the smear layer and possibly the outer layer of the sound tooth structure and has an etching pattern similar to that produced by inorganic acids ($H_3PO_4$, $HNO_3$).

The organic acids employed in the method of the invention seem to provide insoluble or low solubility chelated products, since the scanning electron microscope (SEM) study reveals a superficial etched surface covered by a featureless, uniform layer of modified debris.

The untreated smear layer and the modified smear layer, on the same specimen of dentine, showed about the same thickness of 3–4 μm when 1M glycolic acid or 1M glycolic acid-salicylic acid mixture were used for conditioning the dentine surface.

The chelation effect may explain the preservation of smear layer and the stability of the modified new layer, but can not explain the 4–5 μm intertubular and 10–500 μm tubular penetration of the adhesive, which was noticed in both of the mentioned specimens.

The penetration process seems to be governed by the chemical affinity and dipole-dipole attraction between organic molecules of the adhesive and organic molecules of the tooth structure and favoured by the similarity in the chemical structure of the three part, tooth-conditioner-adhesive.

The conditioners and adhesive monomers which contain in their molecules one but preferably two or more functional groups, in common with the proteins of the organic phase of the tooth, seem to produce the strong and durable bonding of polymeric restorative materials (Table 2, infra). The present inventive method of conditioning is based on this principle.

The organic acids employed in the method of the invention have in common with the proteins two functional groups such as hydroxy and carboxyl or amino and carboxyl. The NTG-GMA monomer has in common with proteins three functional groups such as hydroxy, substituted amino and carboxyl.

These three functional groups are responsible for the hydrophylicity and the polarity of the monomer and perhaps for its chemical affinity and dipole-dipole attraction to the organic phase of the tooth structure.

Adhesiveness is a selective property based on the chemical affinity and similarity between adherent and adhesive. For example, there are specific adhesives for cellulosic materials, metals, glass or ceramics.

Based on the same principle the NTG-GMA or a similar monomer seem to be essential for adhesion to the tooth structure. The monomer of B-solution may differ, since it plays perhaps only the role of a crosslinking agent and eventually the role of carrier for free-radical initiators.

The organic moiety of the chelated product as well as the new orientation of the proteinic molecules of the modified smear layer, intertubular tissue, dentinal fluid and inner lining of dentinal tubules, may constitute the premise for the subsequent chemical affinity and dipole-dipole attraction of the organic molecules of the adhesive, respective, the premise for a good penetration and a true adhesion by secondary bonds (hydrogen and Van-der-Waals).

The penetration of adhesive solution may be either a diffusion by asmosis or diffusion by capillary action or both.

The diffusion by osmosis refers to the movement of the adhesive solution across the modified smear layer, which may play the role of membrane, from the region of high concentration of organic molecules (adhesive layer) to the region of low concentration (the tooth structure). The diffusion by capillary action refers to the tendency of liquids, such as, adhesive solutions, to flow into the narrow spaces due to the chemical attractive forces.

Based on the above consideration, the mechanism of bonding the polymeric restorative materials to the enamel and dentine conditioned with the present inventive polyfunctional organic acids can not be simply micromechanical retention but rather micromechanical associated with true adhesion based on secondary bonds (hydrogen, Van-der-Waals).

This mechanism is supported by the high bond strength values (see Table 2) and by the imformations provided by SEM study such as: the hybrid layer of 8–10 μm involving 3–4 μm modified smear layer and 4–5 μm intertubular tissue, the long polymeric tags of 10–500 μm, well attached to the walls of the tubules, the lack of funnel shape of upper end of the tags, the minutly attachment of the adhesive to the superficial etched enamel surface.

In highly preferred embodiment of the invention, the salicylic acid is added to the α-hydroxy acids, to impart a bacteriostatic effect.

The following preparations and examples show the manner and process of making and using the invention and show the best mode contemplated by the inventor, but are not to be construed as limiting the scope of the invention.

METHOD FOR PREPARING THE SPECIMENS AND FOR TESTING THE SHEAR BOND STRENGTH (SBS).

Three types of specimens were prepared for testing shear bond strength; dentin, enamel and dentin-enamel (2:1 dentin-enamel ratio).

The dentin specimens were prepared by removing the occlusal site and ⅔ of the root of molars, and embedding the crown in polymethylmethacrylate, (PMMA) with occlusal face at the same level with the polymer. The rectangular specimens obtained, (12×15×5 mm) were wet polished on silicon carbide paper, 320 grit, until the surface of the specimen (dentin and PMMA) was flat.

The enamel specimens were prepared by embedding incisors in PMMA (using the same plastic molds of 12×15×5 mm) with the flattest site at the same level with the polymer, and then by wet polishing the surface on silicon-carbide paper 600 grit until a flat surface was obtained.

The dentine-enamel specimens were prepared by sectioning vertically premolars, through the cusps, embedding each half on the way described above, and then wet polished on silicon-carbide paper 320 grit until a flat surface was obtained.

After polishing, the specimens were washed until no grinding particles could be seen on the surfaces, and then dried with a compressed air stream.

The tooth specimen surface (dentin, enamel or dentin-enamel) was conditioned with an aqueous solution of the hydroxy or amino acid, by rubbing the surface with a minisponge or a brush, for 10 seconds and then leaving a fresh layer of conditioner for an additional time of 20 seconds. After washing (10 sec.) and drying (10 sec.), with a compressed air stream, the bonding surface area of 3 mm diameter was delimited by application of a hole punched scotch-tape (0.18 mm thickness).

The adhesive (acetonic solutions A and B of Tenure® or All Bond® bonding systems) was dropped on the surface from the tip of a brush, and before the acetone was evaporated another drop was applied. After 60 seconds (the time for penetration), the acetone and excess of adhesive was removed with a gentle compressed air stream. A small ball of composite e.g. Valux, P50® (3M Co.) or PostCom II®

(Pentron Co.) was applied over the glossy, uniform adhesive layer, and tapped for 10 seconds in order to remove entrapped air and to improve the adaptation of the underlying adhesive to the tooth surface. This first layer of composite of about 0.5 mm thickness, was cured for 20 seconds, using a visible-light curing lamp (Optilux 400®), Demetron Res. Corp. with 600 mw/cm$^2$ intensity. A rubber ring, 3.5 mm diameter and 1–1.5 mm high, was fixed over the first cured layer of composite, filled up with the same composite and cured from the top for 20 seconds.

After removing the rubber ring and the Scotchtape®, the composite rod was cured again 10 seconds from each two cross-lateral directions. The small rod of composite of about 1.5–2 mm high, served only as a support for the knife edge of the plunger, during the shear bond strength test.

The prepared specimens were stored in water at 37° C. for 24 hours. Some specimens were tested after thermocycling (125 cycles at 5° to 55° C., 30" delay).

The shear bond strength test was performed using an Instron Universal Testing Machine (Instron Corp. Canton, Mass.).

Before testing, the specimen was attached with its flat surface to the flat surface of the plunger and tightly held in a vice, in this aligned position.

In order to avoid friction during the test, a plastic sheet of 0.13 mm thickness was interfered between the specimen surface and plunger surface, the specimen was well pressed against the plunger and then the plastic sheet was pulled out. The shear force was applied parallel to the bonding surface through the smooth knife edge 0.3 mm thickness of the flat site of the plunger, with a cross-head speed of 0.5 mm/min (0.02 inch/min). Based on the recorded load and the bonding area, the shear bond strength was calculated in psi and MPa and listed in Table 2. The standard deviation (SD) in MPa and the range of the values are also listed.

The debonding occurred at the tooth-adhesive interface.

The dentin fracture as well as the composite fracture occurred only as a consequence of debonding, when the specimens were over-loaded, respective when the loading continued after the failure, even for 1–2 seconds.

The polyfunctional organic acids were used in aqueous solutions or in aqueous saturated salicylic acid solution (0.22%). (See Table 2).

All solutions are in molar concentrations of 0.5M, 1M or 2M and their corresponding weight percentages are specified in parenthesis. The corresponding pH-values are also indicated. The symbols of polyfunctional organic acids e.g., L (lactic), G (glycolic) associated with the symbol S(salicylic) indicates that the solutions are made using aqueous saturated salicylic acid solution instead of distilled water.

The composite restorative materials used were the commercially available Valux® and P50® (3M Co.) or PostCom II® (Generic Pentron Co.). The adhesive was Tenure® "primer" or All Bond® "primer".

EXAMPLE 1.

Salicylic acid (S) in aqueous saturated solution (0.22% w) with a pH=2.34 was used for conditioning the dentine and the shear bond strength value of 20.24 MPa proved that even in such a low concentration it is a better conditioner then inorganic acids conditioners ($HNO_3$ 2.5% and $H_3PO_4$ 10%) of Tenure® and All Bond® systems. (See Table 2, below).

After thermocycling the shear bond strength value was 19.36 MPa.

EXAMPLE 2.

L-Lactic (L) acid in water solutions of 0.5M (4.5%), 1M (9%) and 2M (18%) with the corresponding pH of 2.02, 1.79, 1.68 was used for conditioning the dentine and shear bond strength (SBS) values of 20.96 MPa, 24.06 MPa and respective 27.03 MPa resulted. Since the three values are in the range of 20–27 MPa with no significant differences among them, the solution of higher concentration of 2M (18%) may be avoided and the mild solutions of 1M(9%) and even 0.5M (4.5%) may serve the scope very well.

L-Lactic acid associated with salicylic acid (SL) in solution of 0.5M and 1M concentration of Lactic acid ($SL_{05}$, $SL_1$), pH=1.95 and respective 1.71, produced SBS values of 23.44 MPa, respective 26.11 MPa, higher then previous, due to a synergistic effect.

The $SL_1$ solution of pH=1.71 with 9% L and 0.22% S may produce a bonding similar with that produced by L2 (18%), pH=1.68 and in addition has a bacteriostatic effect on the treated surface.

$SL_1$ solution provided a SBS value of 21.32 MPa (range 16.38–32.75 MPa) on dentine after thermocycling.

Using the same solution ($SL_1$) for conditioning enamel and enamel dentine surfaces, the SBS values were 24.24 MPa and respective 23.41 MPa, only slightly lower that the value for dentine (26.11 MPa).

L-Lactic acid (α-hydroxypropionic-acid) is optically active due to its asymmetrical molecule and for the same reason it has a high polarity favourable for dipole-dipole attraction to the proteinic molecules of the tooth structure which also have a high polarity.

EXAMPLE 3.

Glycolic acid (G) in water solution of 0.5M (3.8%), 1M(7.6%) and 2M (15.2%) with pH=1.95, 1.82 and respective 1.56 was used for conditioning the dentine and SBS values resulted were 24.42 MPa, 26.30 MPa and respective 26.72 MPa, higher and closer each other than the values for the corresponding solutions of lactic acid. In association with salicylic acid ($SG_{05}$, $SG_1$) the results are not too different (22.85 MPa, 26.90 MPa).

After thermocycling the 2M solution (G2) produced 24.90 MPa SBS slightly lower than before thermocycling. The 1M solution of glycolic acid in association with salicylic acid (SG1) used for conditioning the enamel and enamel-dentine resulted in SBS values of 24.25 MPa and respective 22.04 MPa slightly lower than for dentine (26.90 MPa).

EXAMPLE 4.

L-Tartaric acid (T) is more acidic than lactic and glycolic acid since contains two carboxyl-groups along two hydroxy-groups. Therefore it was used in aqueous solutions of 0.5 and 1 molar concentrations and also in 0.5M solution in saturated aqueous salicylic solution. The pH is 1.57 for T 0.5M, 1.36 for T 1M, 1.53 for ST 0.5M. The SBS values were 22.83 MPa, 28.03 MPa and respective 25.51 MPa.

EXAMPLE 5.

Gluconic acid (Gl) was used in 0.5M (9.8% w) concentration with pH=1.86 for conditioning the dentine and the SBS value of 26.90 MPa (range 23.93–29.60 MPa) is similar with that resulted for glycolic acid 1M (7.6% w).

EXAMPLE 6.

Glucuronic acid (Gr) in concentration of 1M (19.4%) with pH=1.60 used for conditioning the dentine and enamel, produced SBS values of 23.84 MPa and respective 22.23 MPa.

EXAMPLE 7.

Galacturonic acid (Glt) in concentration of 1M (19.4%) with pH=1.53 used for conditioning the dentine and enamel produced SBS values of 23.13 MPa and respective 26.11 MPa.

EXAMPLE 9.

Aspartic acid (Asp) was used in saturated aqueous solution with 0.04M (0.50–0.53% w) concentration, pH=2.97, for conditioning the dentine and the SBS value of 23.51 MPa is similar with that produced by $SL_{05}$, $Gr_1$, or $Glt_1$, but the range of values (13.86–34.01 MPa) is very large, denoting a high dependence of the particular tooth structure.

EXAMPLE 10.

Glutamic acid (Gt) was used in saturated (0.12M, 2.05% w) aqueous solution, pH=3.20, for conditioning the dentine and the SBS value was 23.21 MPa.

TABLE 1

| | Symbol | Conditioner | Formula | Exponent of Acidity | |
|---|---|---|---|---|---|
| | | | | $pka_1$ | $pka_2$ |
| | | INORGANIC ACIDS | | | |
| | | Nitric acid | $HNO_3$ | 3.37 | |
| | | Phorphoric acid | $H_3PO_4$ | 2.12 | |
| | | HYDROXYCARBOXYLIC ACIDS | | | |
| 1 | G | Glycolic acid | $CH_2(OH)COOH$ | 3.83 | |
| 2 | L | L-Lactic acid | $CH_3CH(OH)COOH$ | 3.08 | |
| 3 | T | L-Tartaric acid | $HOOC-CH(OH)-CH(OH)COOH$ | 2.93 | 4.23 |
| 4 | S | Salicylic acid | $C_6H_4(OH)COOH$ | 2.97 | |
| 5 | Gl | D-Gluconic acid | $HOCH_2(CHOH)_4-COOH$ | | |
| 6 | Gt* | D-Glucuronic acid | | | |
| 7 | Glt* | D-Galacturonic acid | | | |
| | | AMINO ACIDS | | | |
| 1 | Gly | Glycine | $H_2N-CH_2-COOH$ | 9.78 | |
| 2 | Asp | DL-Aspartic acid | $HOO-CH(NH_2)-COOH$ | 3.86 | 9.82 |
| 3 | Gt | L-Glutamic acid | $HOOC-CH_2CH_2-CH(NH_2)-COOH$ | 4.07 | 9.47 |

*stereoisomers

The high value of SBS for enamel (26.11 MPa) in comparison with that produced by glucuronic acid (22.23 MPa) can not be explained only by the difference in pH which is 1.53 and respectively 1.60 but rather by the disposition of the hydroxyl-groups which is different for the two stereoisomers with the same brut formula ($C_6H_{10}O_7$). Once again, the influence of the functional organic groups in the conditioning process and further in adhesion, is evident.

EXAMPLE 8.

Glycine (Gly) was used in aqueous solution of 1M (7.5%) concentration, with pH=6.36 for conditioning the dentine, and the SBS value produced, 12.63 MPa is very different from the values showed by all the other 9 polyfunctional organic acids tested and their combinations with salicylic acid. It is known that glycine as well other $\alpha$-amino acid can chelate metals and the chelated products are very stable and insoluble in water. An explanation for the poor conditioning effect may be the insolubility of chelated calcium and the higher value of pH (6.36) which entails a low capacity of dissolving the hydroxy-apatite which is suppose to occur prior or simultaneously with chelation process. EDTA, also an $\alpha$-amino acids, even at pH=7.4 is able to produce an etching pattern similar with that produced by inorganic acids, because its chelated products are very soluble such as it is possible that solubilization of hydroxy-apatite, chelation of calcium and solubilization of chelated calcium occur simultaneously.

TABLE 2

DENTIN BONDING

| No | Cond. | Concentration M | % w | pH | Shear Bond Strength psi | MPa | SD | n | range | Adhesive |
|---|---|---|---|---|---|---|---|---|---|---|
| 1 | Tenure ® | | | | 2654 | 18.30 | 4.05 | 9 | 13.23–24.56 | Tenure ® dry A + B |
| 2 | Tenure ® | | | | 2675 | 18.45 | 3.15 | 8 | 14.05–22.36 | Tenure ® dry. A + B brushing |
| 3 | $H_3PO_4$ | 1.0 | 10.0 | 1.0 | 1499 | 10.34 | 2.81 | 11 | 5.04–14.49 | All Bond. A + B, dry |
| 4 | $H_3PO_4$ | | | | 2420 | 16.69 | 6.35 | 12 | 9.13–26.45 | All Bond. A + B + A, damp |
| 5 | $H_3PO_4$ | | | | 1320 | 9.10 | 3.94 | 9 | 5.04–16.38 | All Bond. (A + B) + A, damp |
| 6 | $H_3PO_4$ | | | | 2659 | 18.34 | 2.34 | 8 | 15.12–22.67 | All Bond. (A + B + A, damp, brushing |

Hydroxy-carboxylic Acids

| No | Cond. | M | % w | pH | psi | MPa | SD | n | range | Adhesive |
|---|---|---|---|---|---|---|---|---|---|---|
| 1 | S | sat | 0.22 | 2.34 | 2935 | 20.24 | 2.76 | 12 | 17.32–25.19 | Tenure A + B |
| 2 | $L_{05}$ | 0.5 | 4.50 | 2.02 | 3039 | 20.96 | 2.47 | 16 | 18.26–25.19 | Tenure A + B |
| 3 | $SL_{05}$ | | | 1.95 | 3399 | 23.44 | 5.07 | 10 | 18.89–33.38 | Tenure A + B |
| 4 | $L_1$ | 1.0 | 9.0 | 1.79 | 3489 | 24.06 | 4.10 | 12 | 18.26–29.92 | Tenure A + B |
| 5 | $SL_1$ | | | 1.71 | 3368 | 26.11 | 2.80 | 12 | 20.47–29.92 | Tenure A + B |
| 6 | $L_2$ | 2.0 | 18.00 | 1.68 | 3919 | 27.03 | 4.28 | 12 | 20.78–35.90 | Tenure A + B |
| 7 | $G_{05}$ | 0.5 | 3.80 | 1.95 | 3541 | 24.42 | 3.02 | 11 | 20.15–30.23 | All Bond A + B |
| 8 | $SG_5$ | | | 1.93 | 3313 | 22.85 | 4.14 | 11 | 18.29–32.12 | All Bond A + B |
| 9 | $G_1$ | | | 1.82 | 3814 | 26.30 | 5.35 | 10 | 18.26–34.01 | All Bond A + B |
| 10 | $SG_1$ | | | 1.78 | 3901 | 26.90 | 5.35 | 10 | 20.47–34.01 | All Bond A + B |
| 11 | $G_2$ | 2.0 | 15.20 | 1.56 | 3874 | 26.72 | 4.57 | 10 | 21.41–38.42 | Tenure A + B |
| 12 | $T_{05}$ | 0.5 | 7.50 | 1.57 | 3310 | 22.83 | 2.40 | 10 | 20.15–27.71 | All Bond A + B |
| 13 | $ST_{05}$ | | | 1.53 | 3699 | 25.51 | 3.17 | 10 | 20.15–28.36 | All Bond A + B |
| 14 | $T_1$ | 1.0 | 15.00 | 1.36 | 4064 | 28.03 | 5.19 | 10 | 20.15–37.79 | All Bond A + B |
| 15 | $Gl_{05}$ | 1.0 | 9.80 | 1.86 | 3901 | 26.90 | 1.90 | 10 | 23.93–29.60 | All Bond A + B |
| 16 | $Gr_1$ | 1.0 | 19.40 | 1.60 | 3457 | 23.84 | 3.82 | 10 | 17.01–31.49 | All Bond A + B |
| 17 | $Glt_1$ | | 19.40 | 1.53 | | 23.13 | 2.76 | 10 | 18.89–28.34 | All Bond A + B |

Amino-carboxylic Acids

| | Cond. | M | % w | pH | psi | MPa | SD | n | range | Adhesive |
|---|---|---|---|---|---|---|---|---|---|---|
| | $Gly_1$ | 1.00 | 7.50 | 6.36 | 1740 | 12.63 | 1.48 | 10 | 10.71–16.38 | All Bond A + B |
| | Asp.sat. | 0.04 | 0.50 | 2.97 | 3409 | 23.51 | 6.38 | 10 | 13.86–34.01 | All Bond A + B |
| | Gt sat. | 0.12 | 8.60 | 3.20 | 3365 | 23.21 | 5.16 | 10 | 16.38–29.60 | All Bond A + B |

After Thermocycling (5°–55° C.)

| | Cond. | M | % w | pH | psi | MPa | SD | n | range | Adhesive |
|---|---|---|---|---|---|---|---|---|---|---|
| | S | | | | 2807 | 19.36 | 2.08 | 8 | 16.38–23.43 | Tenure A + B |
| | $SL_{05}$ | | | | 3025 | 20.86 | 3.32 | 12 | 16.38–27.08 | Tenure A + B |
| | $SL_1$ | | | | 3091 | 21.32 | 4.26 | 12 | 16.38–3275 | Tenure A + B |
| | $L_2$ | | | | 3213 | 22.16 | 4.06 | 12 | 17.01–30.55 | Tenure A + B |
| | $G_2$ | | | | 3601 | 24.90 | 2.39 | 12 | 21.41–30.86 | Tenure A + B |

TABLE 2-continued

ENAMEL BONDING

| | Concentration | | | Shear Bond Strength | | | | | |
|---|---|---|---|---|---|---|---|---|---|
| No Cond. | M | % w | pH | psi | MPa | SD | n | range | Adhesive |
| Hydroxy-carboxylic Acids | | | | | | | | | |
| $SL_1$ | | | 1.71 | 3515 | 24.24 | 2.44 | 10 | 20.15–28.34 | All Bond A + B |
| $SG_1$ | | | 1.78 | 3516 | 24.25 | 2.30 | 12 | 21.41–29.60 | All Bond A + B |
| $ST_{05}$ | | | 1.53 | 2778 | 19.16 | 5.95 | 10 | 11.34–30.86 | All Bond A + B |
| $ST_1$ | | | 1.31 | 3251 | 22.42 | 2.88 | 10 | 18.89–25.82 | All Bond A + B |
| $Gr_1$ | | | 1.60 | 3223 | 22.23 | 4.30 | 10 | 15.75–29.60 | All Bond A + B |
| $Glt_1$ | | | 1.53 | 3786 | 26.11 | 4.87 | 12 | 20.15–36.53 | All Bond A + B |

ENAMEL-DENTIN BONDING

| | Concentration | | | Shear Bond Strength | | | | | |
|---|---|---|---|---|---|---|---|---|---|
| No Cond. | M | % w | pH | psi | MPa | SD | n | range | Adhesive |
| Hydroxy-carboxylic Acids | | | | | | | | | |
| $SL_1$ | | | 1.71 | 3394 | 23.41 | 3.48 | 11 | 20.15–32.12 | |
| $SG_1$ | | | 1.78 | 3196 | 22.04 | 5.03 | 10 | 17.01–32.12 | |
| $ST_{05}$ | | | 1.53 | 3161 | 21.80 | 3.01 | 10 | 18.89–28.82 | |
| $ST_1$ | | | 1.31 | 3176 | 21.91 | 3.30 | 10 | 17.66–26.77 | |

What is claimed is:

1. A process to obtain a strong and durable adhesive bond between a tooth structure and a polymeric material, which comprises;

mechanically preparing a tooth surface to receive the polymeric material, whereby a smear layer on the surface is formed; and applying to the smear layer, a conditioner which comprises a dilute aqueous solution of an organic carboxylic acid selected from the group consisting of hydroxy and amino carboxylic acids; and adhering to the conditioned and mechanically prepared tooth surface a polymeric material.

2. The process of claim 1 wherein the application to the smear layer comprises rubbing the conditioner on the smear layer for 5 to 10 seconds followed by allowing the conditioner to remain on the rubbed surface for 15 to 20 seconds.

3. The process of claim 1 wherein the conditioner is selected from the group of formula:

wherein R is an aliphatic or aromatic hydrocarbon radical; X represents a hydroxy, primary amino or secondary amino group; and Y is hydrogen, alkyl, hydroxy-substituted alkyl, amino-substituted alkyl or carboxy-substituted alkyl.

4. The process of claim 3 wherein the conditioner is selected from the group consisting of α-hydroxy carboxylic acids and α-amino carboxylic acids.

5. The process of claim 3 wherein the conditioner is in aqueous solution of 0.5–2 molar concentration with a pH of 1.2–3.5.

6. The process of claim 1 wherein the conditioner is selected from the group consisting of salicylic acid, lactic acid, glycolic acid, tartaric acid, gluconic acid, glucuronic acid, galacturonic acid, glycine, aspartic acid and glutamic acid.

* * * * *